United States Patent
Salmon et al.

(10) Patent No.: US 6,202,242 B1
(45) Date of Patent: Mar. 20, 2001

(54) LIGHT EMITTING ELECTRIC TOOTHBRUSH

(75) Inventors: D'Miles E. Salmon, Hong Kong (HK); De Anne M. Ambriz, Alameda, CA (US)

(73) Assignee: Zephyr Design, Inc., Alameda, CA (US)

( * ) Notice: Subject to any disclaimer, the term of this patent is extended or adjusted under 35 U.S.C. 154(b) by 0 days.

(21) Appl. No.: 09/369,027

(22) Filed: Aug. 4, 1999

Related U.S. Application Data

(60) Provisional application No. 60/117,731, filed on Jan. 29, 1999.

(51) Int. Cl.[7] .................................................. A61C 17/22
(52) U.S. Cl. ........................... 15/22.1; 15/105; 15/167.1; 362/109; 433/29
(58) Field of Search ........................ 15/22.1, 105, 167.1; 362/109, 119, 120, 804; 433/29

(56) References Cited

U.S. PATENT DOCUMENTS

| | | | |
|---|---|---|---|
| 1,373,388 | * 3/1921 | Warren | 362/109 |
| 3,261,978 | 7/1966 | Brenman | 15/105 |
| 3,667,454 | * 6/1972 | Prince | 15/22.1 X |
| 4,253,212 | 3/1981 | Fujita | 15/167.1 |
| 4,662,947 | * 5/1987 | Hopkins | 15/105 X |
| 4,719,660 | * 1/1988 | Hopkins | 15/105 |
| 4,779,173 | 10/1988 | Carr et al. | 362/109 |
| 5,030,090 | 7/1991 | Maeda et al. | 433/29 |
| 5,160,194 | 11/1992 | Feldman | 362/109 |
| 5,306,143 | * 4/1994 | Levy | 433/29 |
| 5,813,855 | 9/1998 | Crisio, Jr. | 433/29 |
| 6,026,828 | * 2/2000 | Altshuler | 15/22.1 X |

* cited by examiner

Primary Examiner—Mark Spisich
(74) Attorney, Agent, or Firm—John S. Christopher

(57) ABSTRACT

A light emitting electric toothbrush and method therefore is disclosed which is intended for use by children, is comprised of a robust high-strength, plastic construction, and employs both light and vibration to assist in the development of suitable dental hygiene skills. In its most fundamental embodiment, the light emitting electric toothbrush comprises a construction including a handle having a bottom end and a top end and a toothbrush shaft mounted to the top end of the handle. The brush shaft is comprised of a plastic resin including a fluorescent colored light refractive additive for optimizing light transmission through the brush shaft. A high intensity light source is mounted within the top end of the handle for generating light and a domed-shaped optical lens is positioned over the high intensity light source for directing the generated light into the brush shaft. Finally, a switched electrical source is included for energizing the light source and the generated light therefrom creates a glowing illumination in the brush shaft for illuminating a dental cavity of a person during brushing of the teeth. In a preferred embodiment, the toothbrush also includes a vibrating motor mounted within the handle for causing the brush shaft to vibrate. The vibrating motor is also energized by the switched electrical source simultaneously with the light source.

20 Claims, 4 Drawing Sheets

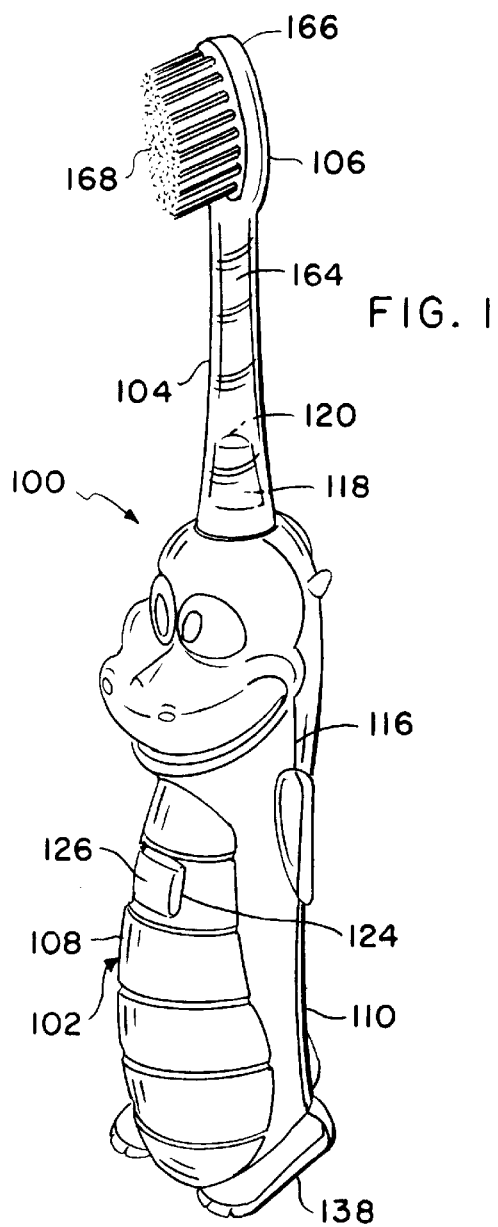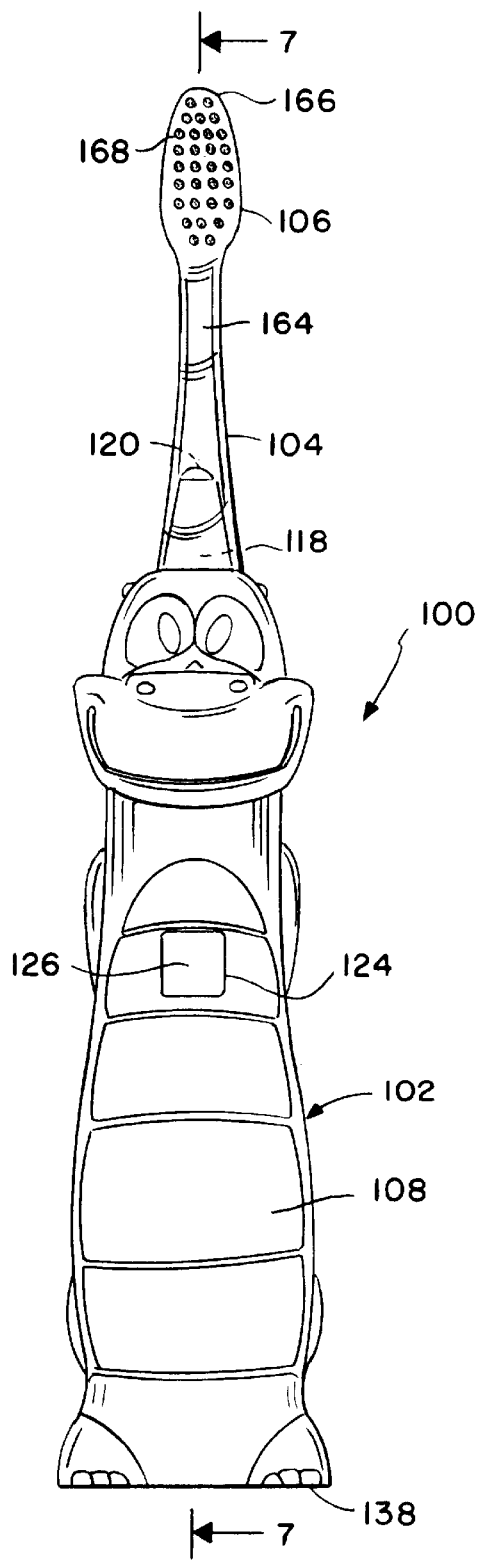
FIG. 1
FIG. 2

LIGHT EMITTING ELECTRIC TOOTHBRUSH

This application claims the benefit of U.S. Provisional Application Ser. No. 60/117,731, filed Jan. 29, 1999.

BACKGROUND OF THE INVENTION

1. Field of the Invention

The present invention relates to dental hygiene. More specifically, the present invention relates to a child's electrical powered toothbrush having an ergonomically sculpted handle, and which projects light and vibrations along a fluorescent-accented brush head to provide improved lighting in and brushing of the oral cavity and to encourage children to practice dental hygiene.

2. Background of the Invention

The best prevention against dental decay and gum disease is a thorough brushing of the teeth and gums following each meal. This action helps to eliminate the plaque buildup that can lead to dental problems. Notwithstanding most everyone in advanced societies possesses a toothbrush, dental cavities or tooth decay and periodontal disease remain a prevalent problem. This fact is especially true among children who tend to dislike the chore of brushing their teeth and may do it improperly or irregularly. Improper dental care can also be attributed to not brushing for a sufficient duration of time, and/or not being able to see plaque or food buildup for effective removal. The cleanliness of toothbrushes is also an issue if the toothbrushes are stored in a horizontal position where the bristles can come into contact with germs and bacteria. Further, dental professionals recommend that toothbrushes be replaced every three-to-six months when the bristles become worn.

The prior art is directed to methods and apparatus for battery operated toothbrushes for use in dental hygiene. Battery operated toothbrushes have been known in the art for assisting individuals in dental cleaning. Many examples of the battery operated toothbrushes are available and several will be briefly discussed at this time.

In a first example, a dental cleaning apparatus has been known which discloses a toothbrush with a light source located within the brush head or handle which emits radiation having a wavelength of 3650 angstrom units. The teeth are brushed with a specially formulated dye which attaches to plaque on the teeth. After brushing, the light source is energized and in combination with a monochromatic filter causes any dye stains within the oral cavity to fluoresce. The teeth can then be rebrushed until the plaque is removed. The dental cleaning apparatus also disclosed the use of a vibrating toothbrush. In a second example, a training apparatus for brushing teeth included a sound emitting device and/or a light emitting device provided in the stem of a toothbrush. The sound and/or light emitting devices were activated by brushing movement of the training apparatus. An electro-conductive movable piece contacted an electrode to complete an electrical circuit which resulted in the generation of the sound or light emitted from the stem of the toothbrush.

In another example, a toothbrush included optical fiber bristles extending longitudinally through the handle portion thereof. The optical fiber bristles were then turned upwardly at the head end of the toothbrush to form the toothbrushing bristles. A bulb end of a flash light was axially connected to the end of the handle of the toothbrush for injecting light into the ends of the optical fibers. The light was then transmitted to the distal end of the fiber bristles at a right angle resulting in loss of much of the transmitted light. Another example discloses an optical toothbrush used for medical treatment including a plurality of narrow fibers connected to a light generating device and extending through a base of the toothbrush. The narrow fibers are bent to form an L-shape and project outward from the base to form a brush. Light emitted from the light generating device is guided into each narrow fiber at its base and projected through the brush tips.

Yet another example discloses a toothbrush with externally illuminated bristles which includes a tubular handle with a shoulder having a light bulb mounted therein. The bulb projects a beam of light across open space onto the external surfaces of the bristles, teeth and plaque when in use. An externally mounted switch used to energize the light bulb is compressed when the toothbrush is held in the brushing position. In a final example, an illuminated toothbrush teaches a light source inserted into a socket at the end of the toothbrush handle for the purpose of illuminating the ends of the filaments. Light emitted from the light source is transmitted by the filaments, a clear plastic toothbrush handle, and the head of the toothbrush. The light from the light source then enters the individual filaments of the respective brush tufts through the bite portion and glows at the end surfaces of the filaments.

The battery operated toothbrushes of the prior art have also been known to incorporate bow spring triggers, high intensity light sources, replaceable toothbrush heads, push-to-operate activation buttons, toothbrush handles comprised of clear resin, and recessed light sources.

Thus, there is a need in the art for a light emitting vibrating electrical powered toothbrush intended exclusively for use by children and including a ergonomically-sculpted handle fashioned in the shape of a fantasy-type character having a high intensity light source combined with a vibrating source for projecting light through and vibrations along a fluorescent-accented shaft and brush head to provide improved lighting of the oral cavity and brushing of the teeth and to encourage children to practice dental hygiene.

SUMMARY OF THE INVENTION

Briefly, and in general terms, the present invention provides a new and improved light emitting electric toothbrush typically used by children during a dental hygiene training phase under the supervision of an adult and prior to their having developed the motor skills necessary to properly brush their teeth. The novel and non-obvious light emitting electric toothbrush exhibits a handle with a toothbrush shaft and brush head mounted thereon. The handle includes an ergonomic design intended for a child's hand and is sculpted in the shape of a fantasy-type character such as, for example, a dragon. The handle can be formed from Acrylonitrile Butabiene Styrene (ABS) and the toothbrush shaft and brush head can be fashioned from a clear plastic light carrying resin combined with a fluorescent-colored light refractive additive which serves to uniformly fill and transmit light throughout the toothbrush shaft and head.

The inventive light emitting electric toothbrush is battery operated and includes a high luminous intensity light source located in the end of the handle. The light source projects light into a replaceable, transparent, colored toothbrush shaft and brush head. It is the toothbrush shaft and brush head that contains the specially formulated light transmitting material (i.e., the fluorescent-colored light refractive additive). A switch located on the handle of the toothbrush is pressed to activate the battery operated circuitry that simultaneously energizes the light source and a vibrating motor employed to cause the toothbrush shaft and brush head to vibrate. The sculpted, ergonomically designed toothbrush handle ensures a more secure grasp and a keen visual interest by children. Further, the vibrating toothbrush head includes thin conventional bristles for improved cleaning action and plaque removal. The high intensity light source creates a glowing illumination of the entire mouth and teeth which results in improved cleaning of the teeth and a fun visual experience for children. The toothbrush stands on its flat base to be stored upright to ensure cleanliness of the bristles. The brush head is removable from the toothbrush handle and can be replaced with a duplicate brush head.

The present invention is generally directed to a light emitting electric toothbrush for use by children, is comprised of a robust high-strength, plastic construction, and employs both light and vibration to assist in the development of suitable dental hygiene skills. In its most fundamental embodiment, the light emitting electric toothbrush comprises a construction including a handle having a bottom end and a top end and a toothbrush shaft mounted to the top end of the handle. The brush shaft is comprised of a plastic resin including a fluorescent colored light refractive additive for optimizing light transmission through the brush shaft. A high intensity light source is mounted within the top end of the handle for generating light and a domed-shaped optical lens is positioned over the high intensity light source for directing the generated light into the brush shaft. Finally, a switched electrical source is included for energizing the light source and the generated light therefrom creates a glowing illumination in the brush shaft for illuminating a dental cavity of a person during brushing of the teeth.

In a preferred embodiment, the toothbrush also includes a vibrating motor mounted within the handle for causing the brush shaft to vibrate. The motor is also energized by the switched electrical source simultaneously with the light source. Further, the vibrating brush head is angled and contoured to maximize the light transmission therethrough. The brush shaft also includes an interlocking receptacle that cooperates with a protuberance formed on a lamp holder molded to the top end of the ergonomically designed handle. The interlocking receptacle includes a groove formed in the domed-shaped optical lens which receives the protuberance formed on the handle. The interlocking receptacle enables the toothbrush shaft to be installed on and removed from the ergonomically designed handle. Finally, the power supply for the battery operated toothbrush is enclosed in a locked compartment located within the flat bottom end of the handle which is accessible for changing batteries as required.

These and other objects and advantages of the present invention will become apparent from the following more detailed description, taken in conjunction with the accompanying drawings which illustrate the invention, by way of example.

BRIEF DESCRIPTION OF THE DRAWINGS

FIG. 1 is a perspective view of a light emitting electric toothbrush of the present invention showing a fluorescent-accented shaft and brush head mounted upon a lamp holder extending from a sculpted fantasy-type character that forms an ergonomically-designed handle of the toothbrush.

FIG. 2 is a front elevational view of the light emitting electric toothbrush of FIG. 1 showing the sculpted handle, the lamp holder, an on-off switch, the fluorescent-accented shaft and brush head, and a flat base.

DESCRIPTION OF THE INVENTION

The present invention is a light emitting electric toothbrush 100 and method specifically designed for use by children during their dental hygiene training phase. The toothbrush 100 employs both light transmission into an oral cavity of a person (not shown) and vibration along the longitudinal axis of a brushing mechanism to assist children in visually inspecting and brushing their teeth. The toothbrush 100 is particularly useful for instructing children in the procedures of dental hygiene by requiring them to utilize both visual and tactile senses prior to their development of the motor skills necessary to execute a thorough brushing.

A preferred embodiment of the light emitting electric toothbrush 100 of the present invention is best shown in FIGS. 1–4. The toothbrush 100 has several main components including a handle 102 and a brushing mechanism comprising a toothbrush shaft 104 and a brush head 106 as shown in FIGS. 1 and 2. The handle 102 is ergonomically-designed for use by children, i.e., designed for little hands. To promote the interest of children in the toothbrush 100 and thus encourage them to practice dental hygiene, the handle 102 can be sculpted into a fantasy-type character that cooperates with the ergonomic design. Any suitable fantasy-type character can be incorporated into the present invention. The preferred embodiment of the present invention employs a multi-colored smiling dragon intended to attract the attention of small children. Mounted above the sculpted handle 102 of the light emitting electric toothbrush 100 is the toothbrush shaft 104 having the brush head 106 positioned at the top thereof as is clearly shown in FIGS. 1–4. The toothbrush shaft 104 and the brush head 106 are integrally connected and are disconnectively attached to the handle 102 as shown in the exploded view of FIG. 7.

Figure 3:
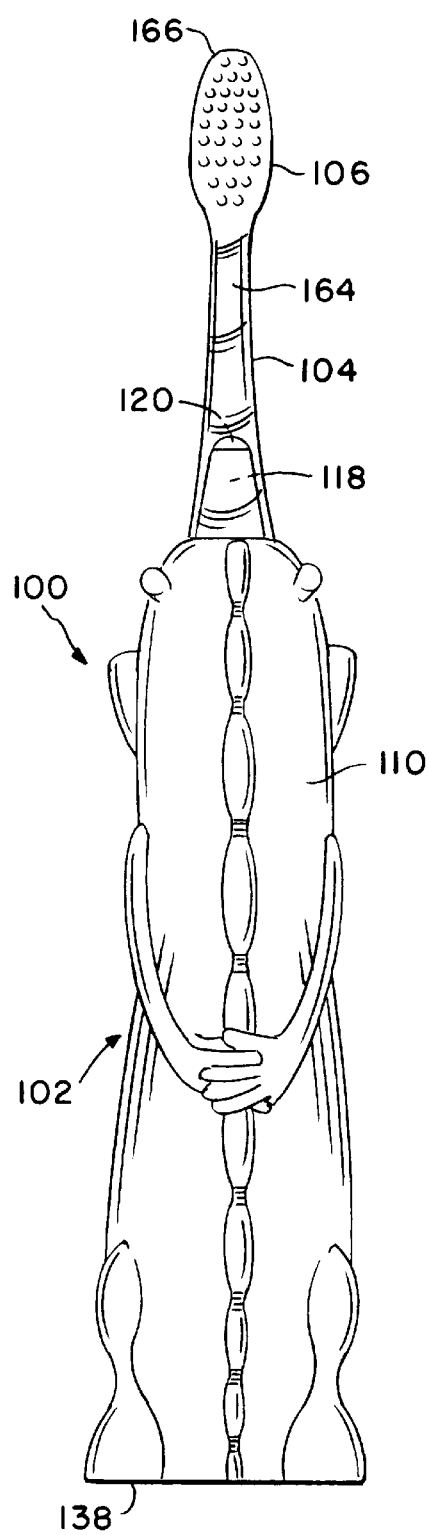
FIG. 3 is a rear elevational view of the light emitting electric toothbrush of FIG. 1 showing the back side of the ergonomically-designed sculpted handle, the lamp holder, the fluorescent-accented shaft and brush head, and the flat base.
Figure 4:
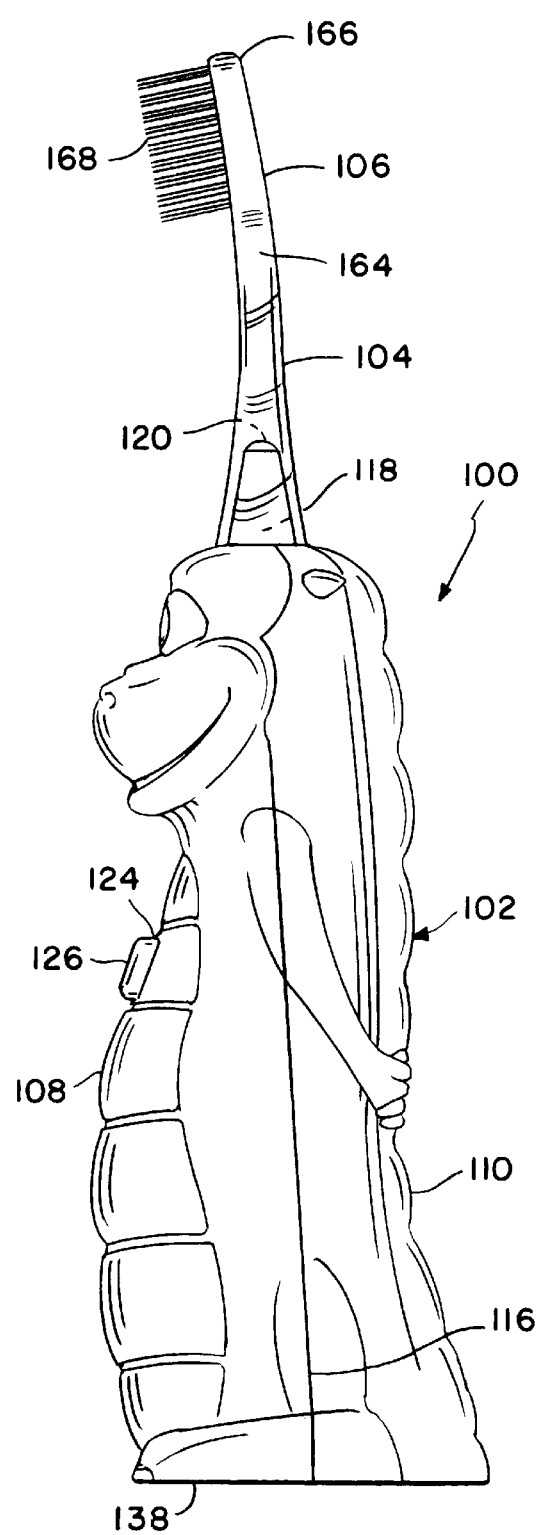
FIG. 4 is a left side elevational view of the light emitting electric toothbrush of FIG. 1 showing the lamp holder positioned beneath the fluorescent-accented shaft and brush head, the flat base, and the left side of the sculpted handle, the right side being a mirror image thereof.
Figure 5:
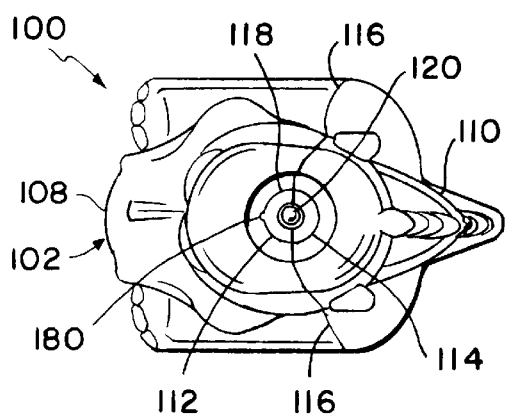
FIG. 5 is a top planar view of the light emitting electric toothbrush of FIG. 1 showing the top of a high intensity lamp and the lamp holder mounted above the ergonomically-designed sculpted handle.
Figure 7:
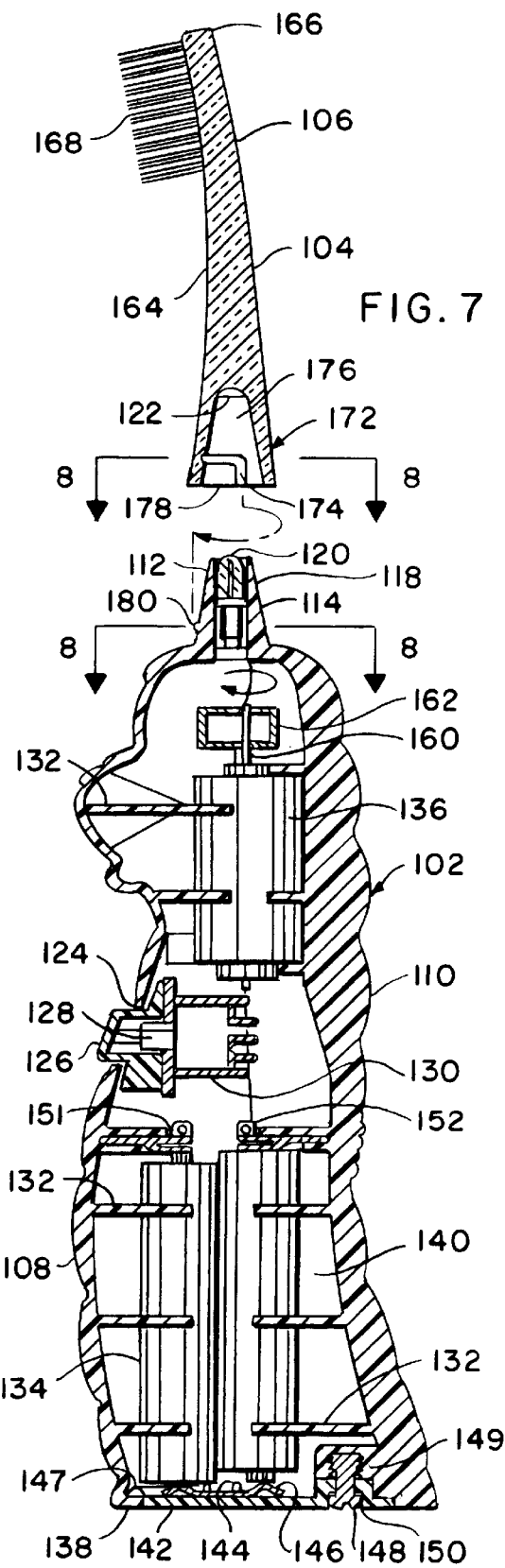
FIG. 7 is a cross-sectional view of the light emitting electric toothbrush of FIG. 1 taken along line 7—7 of FIG. 2 showing the interior of the sculpted handle including the battery compartment, the on-off switch, a vibrating motor, the lamp holder, the high intensity lamp, and the fluorescent accented shaft and brush head exploded away from the sculpted handle.

The following is a description of the ergonomically designed handle 102 of the present invention. Notwithstanding the exterior cosmetic sculpting selected for the particular toothbrush 100, the handle 102 includes a front body portion 108 and a rear body portion 110 as is shown in FIG. 4. Both the front body portion 108 and the rear body portion 110 are fashioned by plastic injection molding from a suitable material such as Acrylonitrile Butabiene Styrene (hereinafter "ABS"). Molded to the top surface of the front body portion 108 is a front upward concave extension 112. Likewise, molded to the top surface of the rear body portion 110 is a mating rear upward concave extension 114 as is best shown in FIG. 7. Thereafter, the front body portion 108 including the front upward concave extension 112 and the rear body portion 110 including the rear upward concave extension 114 are ultrasonically bonded together along an interface line 116 as best shown in FIG. 4. Thus the front body portion 108 and the rear body portion 110 are intended to be permanently sealed.

Figure 9:
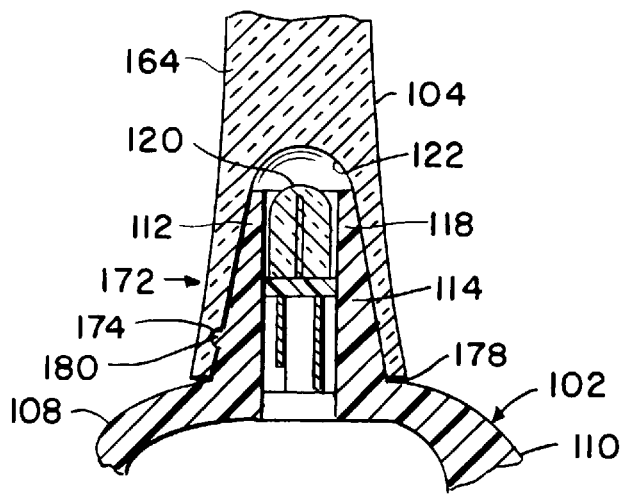
FIG. 9 is an enlarged partial view of the light emitting electric toothbrush of FIG. 1 showing the high intensity light source and lamp holder fitted inside the domed lens of the fluorescent-accented shaft, the components locked together with the groove and nipple attachment mechanism of FIG. 8.

The mating of the front upward concave extension 112 to the rear upward concave extension 114 provides a generally upward extending, truncated, conical shape which serves as a lamp holder 118 as shown in FIG. 9. A high intensity, vacuum bi-pin lamp 120 incorporated into a T1 envelope is mounted in the lamp holder 118. The high intensity lamp 120 is positioned within the lamp holder 118 so that 2.5 millimeters (mm) of the lamp 120 extend upward and outward from the lamp holder 118 as shown in FIGS. 7 and 9. This positioning of the lamp 120 within the lamp holder 118 ensures that an adequate amount of light will be (a) projected into a domed-shaped optical lens 122 located in the bottom of the toothbrush shaft 104 and also (b) projected into the brush shaft 104 and the brush head 106. The high intensity lamp 120 preferably should be rated at 3.0 volts drawing within the range of aproximately 0.330-to-0.450 amperes maximum and include a C2R filament, an MSCP (Measurement of Light in Mil Candle Power) of 1.02 and have a life expectancy of a minimum of 60 life hours at full load before the C2R filament burns out. The high intensity lamp 120 is manufactured by and available from Precision Lighting or Whamco Lighting, both of Santa Rosa, Calif.

A penetration 124 is formed through the front body portion 108 of the ergonomically designed handle 102 to accommodate a switch cap 126 as best shown in FIG. 7 but also shown in FIGS. 1, 2 and 4. The switch cap 126 is located over an actuating plunger 128 of a two-position (on/off) button switch 130 that is mounted to structural ribbing 132 molded to the inside surfaces of the front body portion 108 and rear body portion 110 (see FIG. 7). The structural ribbing 132 is comprised of the same ABS material as the remainder of the handle 102. The switch cap 126 and the button switch 130 including associated brackets are mounted to the structural ribbing 132 by any suitable means such as, for example, by screws. The switch cap 126 is injection molded and comprised of a soft material such as silicone or synthetic rubber to provide a comfortable feel and a watertight seal over the two-position button switch 130. The two-position button switch 130 serves to apply electrical potential from a direct current (d.c.) power supply 134 to the high intensity lamp 120 and to a vibrating motor 136. The vibrating motor 136 is also located within the handle 102 and is also supported by and fastened to the structural ribbing 132 molded to the inside surfaces of the handle 102.

Figure 6:
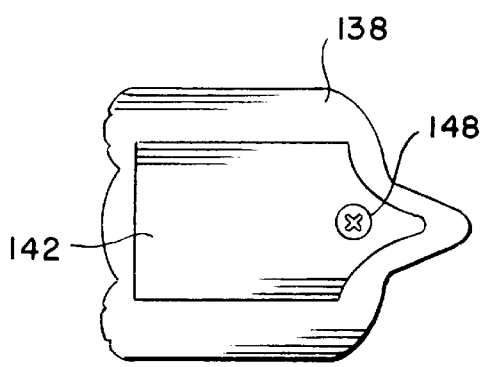
FIG. 6 is a bottom planar view of the light emitting electric toothbrush of FIG. 1 showing the flat base and a removable battery door for providing access to a battery compartment.

The ergonomically designed handle 102 includes a flat bottom 138 as shown in FIGS. 6 and 7 which enables the light emitting electric toothbrush 100 to stand upright for storage. The flat bottom 138 also assists in maintaining cleanliness in the brush head 106 since there is a higher probability of avoiding exposure to debris and bacteria when the toothbrush 100 is in the vertical position. The d.c. power supply 134 comprised of two AAA cell alkaline batteries (each generating 1.5 volts d.c.) is located within a battery compartment 140 inside the ergonomically designed handle 102 as is best shown in FIG. 7. The battery compartment 140 is accessible through a hinged battery door 142 formed in the flat bottom 138 best shown in FIG. 6. The battery door 142 is injection molded from a rigid material such as, for example, ABS and includes two ABS pins 144 formed on the inside of the battery door 142 for securing a battery contact plate 146 thereto as shown in FIG. 7. The battery contact plate 146 includes a pair of penetrations (not shown) through which the two ABS pins 144 pass. Once the battery contact plate 146 is positioned over the ABS pins 144, the two ABS pins 144 formed on the inside of the battery door 142 are melted down in a typical heat staking operation as is known in the art. This procedure ensures that the battery contact plate 146 is securely held in position.

The battery door 142 is hinged on one end thereof and slides into a pair of slots 147 located in the front body portion 108 and swings to close onto the rear body portion 110. A door securing screw 148 is employed to secure the hinged battery door 142 to a threaded body boss 149 molded to the rear body portion 110 to prevent children from accessing the battery compartment 140. In particular, the door securing screw 148 is captivated within the hinged battery door 142 as shown in FIG. 7. The hinged battery door 142 includes a penetration 150 formed therein through which the door securing screw 148 passes. The screw 148 is press-fitted through the penetration 150 in the battery door 142. The penetration 150 in the battery door 142 has a diameter smaller than the diameter of the threads but larger than the diameter of the shaft of the door securing screw 148 to enable movement of the screw 148. This design enables the screw 148 to secure the closure of the battery door 142 but when the threads are disengaged, the door securing screw 148 will remain captured within the penetration 150 of the battery door 142. This design prevents the door securing screw 148 from becoming a "small part" hazard to small children. Removal of the door securing screw 148 requires forcing the screw 148 back through the penetration 150.

The interior construction of the ergonomically designed handle 102 is best shown in FIG. 7. The ABS structural ribbing 132 is clearly shown for supporting the d.c. power supply 134, the two-position button switch 130, and the vibrating motor 136. The electrical circuitry of the toothbrush 100 is energized by the two AAA cell alkaline batteries of the power supply 134 generating a total of 3.0 volts. Mounted directly above the battery compartment 140 is a positive contact plate 151 and a negative contact plate 152. The positive contact plate 151 is in electrical communication with the positive terminal of a first of the two AAA cell alkaline batteries of the power supply 134. Likewise, negative contact plate 152 is in electrical communication with the negative terminal of a second of the two AAA cell alkaline batteries of the power supply 134. In addition, the battery contact plate 146 shown at the bottom of the battery compartment 140 in FIG. 7 electrically connects the negative terminal of the first AAA cell alkaline battery to the positive terminal of the second AAA cell alkaline battery. Thus, the two AAA cell alkaline batteries of the power supply 134, the positive contact plate 151, the negative contact plate 152 and the battery contact plate 146 form a series connection as is shown in FIG. 10.

The two position button switch 130 is clearly shown mounted to the structural ribbing 132 in FIG. 7. The actuating plunger 128 extending from the switch 130 is spring-loaded and can be operated by pressing on the switch cap 126. The switch 130 is clearly shown in FIG. 10 as being connected in series with the two AAA cell alkaline batteries of the power supply 134. Thus, operation of the switch 130 will apply electrical power to the high intensity lamp 120 and the vibrating motor 136. The two position button switch 130 can be any suitable two position, spring-loaded, press-to-operate switch having contacts that are rated to provide electrical power to the high intensity lamp 120 and to the vibrating motor 136, simultaneously. It is clear from FIG. 10 that the high intensity lamp 120 and the vibrating motor 136 are parallel connected so that the 3.0 volt potential generated by the power supply 134 is applied to both electrical loads. Thus, the voltage between potential points 154 and 156 shown on FIG. 10 is 3.0 volts. The high intensity lamp 120 is rated at 3.0 volts drawing from 0.330-to-0.450 amperes and thus is connected directly across potential points 154 and 156.

The vibrating motor 136 can be, for example, a Mabuchi motor having a variable input voltage ranging from (1.5–3.0) volts d.c. depending upon the desired motor speed. This motor is manufactured by Mabuchi Motors Ltd. in Japan and can be ordered using stock number #FA-130RA-2270. As can be seen in FIG. 7, the vibrating motor 136 is mounted within and supported by the structural ribbing 132. It is noted that an electrical resistor 158 is placed in series with the vibrating motor 136 to increase the resistive load therein. The higher resistive load results in a larger voltage drop in the parallel leg containing the vibrating motor 136. If the electrical resistor 158 is properly sized, the voltage potential across the motor can be dropped from 3.0 volts d.c. to 1.5 volts d.c. This voltage reduction can be accomplished when the electrical resistor 158 has a resistance of 5.1 ohm for dissipating ¼ watt of power. This example voltage reduction reduces the speed of the vibrating motor to 7000 RPM. Thus, it can be seen that when the two position button switch 130 is actuated, the high intensity lamp 120 and the vibrating motor 136 are energized simultaneously.

Figure 10:
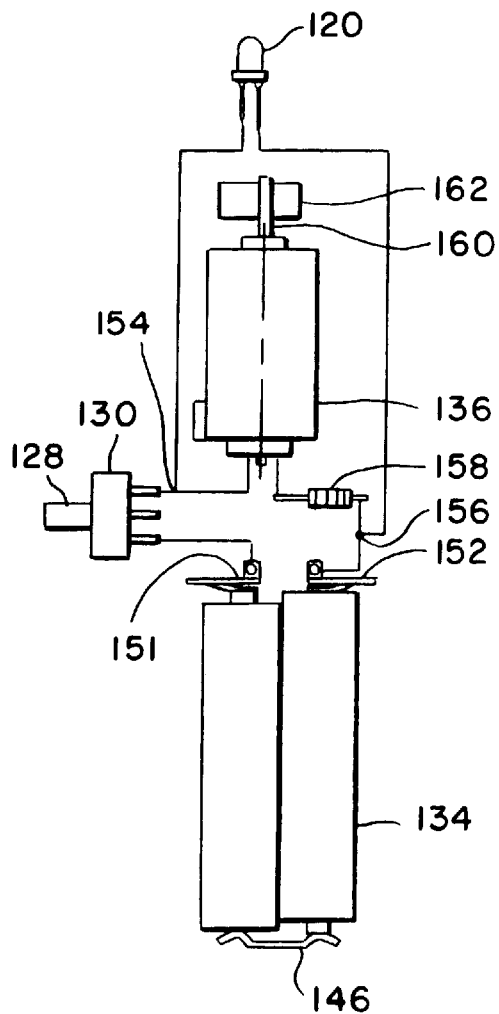
FIG. 10 is a schematic diagram of the light emitting electric toothbrush of FIG. 1 showing the electrical components including a Direct Current (DC) power supply, the on-off switch, the high intensity lamp and vibrating motor wired in parallel, and a resistive component in line with the vibrating motor.

The vibrating motor 136 includes an output shaft 160 as shown in FIGS. 7 and 10. The output shaft 160 rotates at the speed determined by the electrical resistor 158, for example, 7000 RPM. Mounted upon the output shaft 160 of the vibrating motor 136 is a cam cylinder 162 as shown in FIGS. 7 and 10. The cam cylinder 162 is mounted off-center and thus causes the output shaft 160 to wobble during rotary motion. Because the output shaft 160 of the motor 136 rotates at a high frequency, i.e., for example, 7000 RPM, a high frequency vibration in the output shaft 160 results. The motor 136, which vibrates because of the off-center cam cylinder 162, transfers the vibrations to the structural ribbing 132, the handle 102, the brush shaft 104 and the brush head 106. Thus, the vibrations created within the handle 102 are transferred to the brush head 106 to assist in cleaning the teeth of the child.

It is noted that the handle 102 is ergonomically designed especially for use by children. In effect, this statement means that the exterior design of the front body portion 108 and the rear body portion 110 are sculpted to fit small hands such as those of children. In particular, FIGS. 1–4 illustrate the overall shape of the handle 102. FIG. 4 is a side elevational view which clearly shows how the front body portion 108 is somewhat convex in shape and the rear body portion 110 is somewhat concave in shape. Because of this design, the concave rear body portion 110 fits conveniently into the palm of a small hand. Likewise, the convex front body portion 108 of the handle 102 is conveniently shaped for wrapping the fingers of a small hand thereabout. Additionally, the switch cap 126 is positioned on the front body portion 108 so that it can be conveniently pressed by the fingers of the child for actuating the two position button switch 130.

The toothbrush mechanism will now be described. The entire toothbrush mechanism is removable from the handle 102 and is comprised of the brush shaft 104, the brush head 106 and the domed-shaped optical lens 122. The brush shaft 104 and brush head 106 are injection molded into an integral unit from a custom mixed polycarbonate material which is a clear plastic light carrying resin identified as Novarex® #7022IR. This material is available from Raycon Industries, Inc. of Sunnyvale, Calif. The Novarex® material has a 22 melt index (referring to the rating for injection molding conditions for heat and pressure factors) and contains a translucent, fluorescent colored additive 164 employed for enhanced light transmission and fill of the clear plastic resin of which the brush shaft 104 and the brush head 106 are comprised. In this situation, the term "fill" means uniform light consistent among the surfaces visualized.

The fluorescent colored additive 164 incorporated into the Novarex® #7022IR material functions as a refracting material for deflecting and carrying light throughout the brush shaft 104 and brush head 106 and to fill the contours thereof. Thus, the fluorescent colored additive 164 reflects and refracts light and transmits the light to the surfaces of the brush shaft 104 and brush head 106. The Novarex® material contains a 7% concentration of the fluorescent colored additive 164 for enhancing the light transmission through the light carrying resin polycarbonate material of the brush shaft 104 and brush head 106. The fluorescent colored additive 164 can be obtained in a plurality of colors from Color Science in Santa Ana, Calif. The stock number for the additive 164 is Color Science #CS1Y704C. In the preferred embodiment of the present invention, the color selected for the fluorescent colored additive 164 was yellow. However, any color of fluorescent colored additive 164 could be utilized as the refracting material.

The brush shaft 104 and brush head 106 are specially designed to include contours and angles that enhance the transmission of light for carrying the light rays from the high intensity lamp 120 to the top 166 of the brush head 106 and angled to reach the back teeth. The aforementioned contours and angles incorporated into the brush shaft 104 can be described as reflecting fillets and radii that enhance light transmission. The contours and angles function as defined reflective and refractive surfaces in optical optimum geometry resulting in uniform light fill of the brush shaft 104 and brush head 106. The fillets are surfaces with specific radii that reflect light transmission. An optimal condition for reflecting light is created by the use of radii with minimum angles. It is not a measurement that creates the effect of light fill and consistency but a condition that is created. The goal is to reduce or eliminate sharp bends. Thus, the larger the angle and the radii, the better the condition for light fill and consistency. Light bounces into and out of the fillets filling the surfaces visualized.

A plurality of bristles 168 are anchored in a known manner to the brush head 106 as is shown in FIGS. 1–4 and 7. The brush bristles 168 are conventional, thin filament bristles having a diameter of approximately 0.15 mm and comprised of a clear nylon material. Formed in the bottom of the brush shaft 104 (and opposite to the end of the brush head 106) is the domed-shaped optical lens 122 shown in FIGS. 7 and 9. The domed-shaped optical lens 122 is a geometric feature of the molded brush shaft 104. The lens 122 is comprised of Novarex® #7022IR polycarbonate material and is a highly polished optical lens. In particular, the lens 122 includes a highly polished SPI/SPE #1 finish which refers to the surface finish on the mold utilized to form the lens 122. As a consequence of the use of this mold rating, the resulting domed-shaped optical lens 122 will be highly polished. The SPI/SPE #1 rating is important as it is a measurement of the surface irregularities measured in microns. The SPI/SPE #1 rating (also known as micro finish) is an industry standard established by the Mold Makers/ Engineers Society of America.

The domed-shaped optical lens 122 is typically referred to as a concave single plano lens. The highly polished surface on the lens 122 creates an optical surface for refracting light rays. Thus, the function of the optical lens 122 is to collect the scattered light rays from the high intensity light source 120 and to direct the light rays into the toothbrush shaft 104 and brush head 106. The illustration in FIG. 9 shows the proximity of the light source 120 to the optical lens 122. The highly polished surface on the lens 122 in combination with the light fill characteristics of the fluorescent colored additive 164 result in improved light fill, light transmission and full glowing illumination of the brush shaft 104 and brush head 106. Consequently, the brush shaft 104 and the brush head 106 are illuminated by the light source 120 and the optical lens 122 so as to light up the dental cavity of the child. This visual assistance helps the child in brushing their teeth and also creates a fun visual experience.

Figure 8:
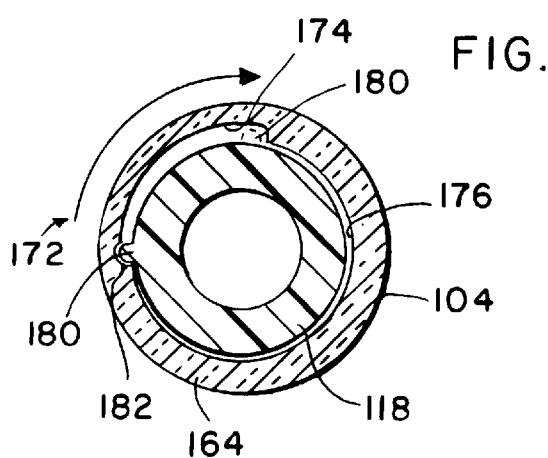
FIG. 8 is an enlarged cross-sectional view of the light emitting electric toothbrush of FIG. 1 taken along line 8—8 of FIG. 7 showing a groove formed within a sidewall of a domed lens of the fluorescent-accented shaft and brush head for receiving a nipple formed on the exterior of the lamp holder for locking the brush head to the sculpted handle.

The brush shaft 104 is mechanically connected to the lamp holder 118 formed at the upper end of the ergonomically designed handle 102 as is best shown in FIGS. 7 and 9. Molded into the bottom of the brush shaft 104 just beneath the highly polished domed-shaped optical lens 122 is an interlocking receptacle 172. The interlocking receptacle 172 includes a groove 174 cut or formed into a sidewall 176 of the conical opening associated with the domed-shaped optical lens 122 as is shown in FIG. 7. The groove 174 is formed in the shape of a right angle with an opening to the groove 174 located at the bottom edge 178 of the brush shaft 104. The groove 174 is positioned and sized to cooperate with a protuberance 180 formed on the side of the lamp holder 118 as shown in FIGS. 7, 8 and 9. The protuberance 180 is molded from ABS onto the front upward concave extension 112 of the lamp holder 118.

As shown in FIG. 7, the opening to the groove 174 formed on the bottom edge 178 of the brush shaft 104 is positioned so as to be aligned with the protuberance 180. The groove 174 formed in the sidewall 176 is forced down over the protuberance 180 extending from the lamp holder 118. The protuberance 180 initially travels upward through a vertical portion of the groove 174. Thereafter, the brush shaft, 104 or alternately the handle 102, is rotated in the appropriate direction to force the protuberance 180 into a horizontal portion of the groove 174.

FIG. 8 is a cross-sectional view taken through the lamp holder 118 but below the high intensity lamp 120 as shown in FIG. 7. In FIG. 8, the protuberance 180 is shown (in phantom) at the top of the vertical portion of the groove 174. Thereafter, the brush shaft 104 (or the handle 102) is appropriately rotated to cause the protuberance 180 to pass through the horizontal portion of the groove 174. Eventually, the protuberance 180 reaches a stop 182 at the end of groove 174 and the brush shaft 104 is now locked to the handle 102 for forming a water tight fit. A sectional view showing the brush shaft 104 locked onto the handle 102 is shown in FIG. 9. Removal of the brush shaft 104 from the handle 102 can be accomplished by reversing the previously described procedure. An alternative interlocking receptacle 172 could include ribbing (not shown) formed within the conical opening on the bottom edge 178 of the brush shaft 104 the cooperates with corresponding ribbing (not shown) formed on the exterior surface of the lamp holder 118. In either scheme, an additional brushing mechanism comprising the brush shaft 104 and the brush head 106 is available for replacement when the brush bristles 168 become worn.

The present invention provides a solution to the problems existing heretofore by providing an easy-to-use, battery operated electric toothbrush 100 that creates a glowing illumination of the mouth to provide improved visibility of the teeth and gums for cleaning food particles therefrom. At the same time, an exciting visual effect is created by both the glow of the material and the sculpted design of the ergonomically designed handle 102 which will encourage children to want to use the toothbrush 100 more frequently. Combined with the light, the vibrating action of the plurality of bristles 168 provides improved teeth cleaning for children who have not yet developed fine motor skills. The high intensity lamp 120 is keep clean by being enclosed within the lamp holder 118 and is therefore not exposed to toothpaste buildup and water.

The brush shaft 104 and brush head 106 are angled and contoured for improved light fill and for reaching back teeth and contains conventional clear, thin bristles 168 for efficient cleaning. The two-position button switch 130 mounted on the handle 102 is easy to actuate and the toothbrush 100 will remain energized until the button switch 130 is pressed again to de-energize it. Thus, the child does not have to continuously press an activation switch while simultaneously attempting to brush their teeth. The toothbrush 100 is stored upright on the flat bottom 138 which minimizes exposure of the bristles 168 to germs and bacteria. The integral brush shaft 104 and brush head 106 can be discarded when the bristles 168 are worn and replaced with an additional brushing mechanism. The batteries of the d.c. power supply 134 are easily replaced by removing the securing screw 148 from the hinged battery door 142. The securing screw 148 also serves as a safety feature by requiring adult supervision to access the power supply 134.

The present invention provides additional novel advantages over other electric toothbrushes known in the art. A main advantage of the light emitting electric toothbrush 100 of the present invention is that it is intended exclusively for use by children and includes an ergonomically-designed handle 102 sculpted into the shape of a fantasy-type character to visually attract the interest of children. The toothbrush 100 includes a high intensity light source 120 combined with a vibrating motor 136 for projecting light through and vibrations along a brush shaft 104 and a brush head 106. Both the brush shaft 104 and brush head 106 contain a translucent, fluorescent colored light refractive additive 164 to provide uniform fill and optimized light transmission therethrough for improved lighting of the oral cavity and brushing of the teeth and to encourage children to practice dental hygiene.

Obviously the invention is susceptible to changes and alterations without defeating its practicability. Therefore, we do not wish to be confined to the preferred embodiment shown in the drawings and described herein. Many other variations are possible, such as, the type or percentage of color additive used for the toothbrush shaft 104 and brush head 106 which can vary from as little as 2% to 25%, and the actual color may vary, such as fuchsia, green, aqua and the like. Different materials or a combination of materials may be used for the injection molding of the handle 102 and the brushing mechanism. Other additives, such as, sparkles or special effects can be added to the ABS plastic for visual and lighting effect. A different fluorescent colored additive 164 or material can be utilized in the toothbrush shaft 104 and brush head 106. Additional lamps 120 or different types of lamps or lighting devices can be employed in the handle 102 and brushing mechanism for improved light fill and decorative effect. Sound effects could also be added to the inventive toothbrush 100.

The design of the handle 102 can vary from the dragon design selected for the present invention but can also adopt other shapes or forms. Different switch mechanisms, motors, resistors and circuit components can be substituted for those appearing in the drawing Figs. The replaceable brushing mechanism and method of attachment can be changed to a threaded type interlocking receptacle 172 or eliminated entirely. Different types of batteries may also be utilized. It is within the design criteria to incorporate a rechargeable unit in combination with the d.c. power supply 134 or, in the alternative, to include appropriate circuitry to enable the use of an alternating current source. Also, additional facets or surface texture or detail may be added to the toothbrush shaft 104, brush head 106 or handle 102 for enhancing light fill and effect.

While the present invention is described herein with reference to illustrative embodiments for particular applications, it should be understood that the invention is not limited thereto. Those having ordinary skill in the art and access to the teachings provided herein will recognize additional modifications, applications and embodiments within the scope thereof and additional fields in which the present invention would be of significant utility.

It is therefore intended by the appended claims to cover any and all such modifications, applications and embodiments within the scope of the present invention. Accordingly,

What is claimed is:

1. A light emitting electric toothbrush comprising:
   a handle having a bottom end and a top end;
   a brush shaft mounted to said top end of said handle, said brush shaft comprised of a plastic resin including a fluorescent colored light refractive additive for optimizing light transmission through said brush shaft;
   a high intensity light source mounted within said top end of said handle for generating light;
   a domed-shaped optical lens positioned over said high intensity light source for directing said generated light into said brush shaft; and
   a switched electrical source for energizing said light source, wherein said generated light creates a glowing illumination in said brush shaft for illuminating a dental cavity of a person.

2. The light emitting electric toothbrush of claim 1 wherein said handle is comprised of Acrylonitrile Butabiene Styrene (ABS).

3. The light emitting electric toothbrush of claim 1 wherein said bottom end of said handle is flat for supporting the toothbrush in an upright position.

4. The light emitting electric toothbrush of claim 1 wherein said brush shaft includes an interlocking receptacle that cooperates with a protuberance formed on a lamp holder molded to said handle.

5. The light emitting electric toothbrush of claim 4 wherein said interlocking receptacle of said brush shaft includes a groove formed in said domed-shaped optical lens.

6. The light emitting electric toothbrush of claim 1 wherein said high intensity light source is mounted within a lamp holder molded to said top end of said handle.

7. The light emitting electric toothbrush of claim 1 wherein said domed-shaped optical lens is a highly polished lens formed within said brush shaft.

8. The light emitting electric toothbrush of claim 1 wherein said switched electrical source includes a push-to-operate switch in series with a direct current electrical source.

9. The light emitting electric toothbrush of claim 8 wherein said direct current electrical source is located within a compartment within the bottom end of said handle.

10. The light emitting electric toothbrush of claim 9 wherein said compartment includes a locking door.

11. The light emitting electric toothbrush of claim 1 wherein said handle is sculpted and ergonomically designed for use by a child.

12. The light emitting electric toothbrush of claim 1 wherein said brush shaft is angled and contoured to maximize light transmission.

13. The light emitting electric toothbrush of claim 1 wherein said handle further includes a plurality of internal ribbing for providing structural support.

14. The light emitting electric toothbrush of claim 1 further including a vibrating motor for causing said brush shaft to vibrate.

15. A light emitting electric toothbrush comprising:
   an ergonomically designed handle having a bottom end and a top end;
   a brush shaft mounted to said top end of said handle, said brush shaft comprised of a light carrying resin including a fluorescent colored light refractive additive for optimizing light transmission through said brush shaft;
   a light source mounted within said top end of said handle for generating light;
   an optical lens positioned over said light source for directing said generated light into said brush shaft;
   a motor mounted within said handle for causing said brush shaft to vibrate; and
   a switched electrical source for simultaneously energizing said light source and said motor, wherein said generated light creates a glowing illumination in said brush shaft for illuminating a dental cavity of a person.

16. The light emitting electric toothbrush of claim 15 wherein said bottom end of said ergonomically designed handle is flat for supporting said toothbrush in an upright position.

17. The light emitting electric toothbrush of claim 15 wherein said optical lens is a highly polished domed-shaped lens formed within said brush shaft.

18. A light emitting electric toothbrush comprising:
   an ergonomically designed handle having a bottom end and a top end;
   a brush shaft mounted to said top end of said handle, said brush shaft comprised of a plastic resin including a fluorescent colored light refractive additive for optimizing light transmission through said brush shaft;
   a high intensity light source mounted within said top end of said handle for generating light;

a domed-shaped optical lens positioned over said high intensity light source for directing said generated light into said brush shaft;

a vibrating motor mounted within said handle for causing said brush shaft to vibrate; and a switched electrical source for simultaneously energizing said light source and said vibrating motor, wherein said generated light creates a glowing illumination in said brush shaft for illuminating a dental cavity of a person.

19. The light emitting electric toothbrush of claim 18 wherein said bottom end of said ergonomically designed handle is flat for supporting the toothbrush in an upright position.

20. The light emitting electric toothbrush of claim 18 wherein said handle is comprised of Acrylonitrile Butabiene Styrene (ABS).

* * * * *